(12) United States Patent
Sawai

(10) Patent No.: US 12,201,505 B2
(45) Date of Patent: Jan. 21, 2025

(54) UNDERPANTS-TYPE DISPOSABLE DIAPER

(71) Applicant: DAIO PAPER CORPORATION, Ehime (JP)

(72) Inventor: Asako Sawai, Ehime (JP)

(73) Assignee: Daio Paper Corporation, Ehime (JP)

( * ) Notice: Subject to any disclaimer, the term of this patent is extended or adjusted under 35 U.S.C. 154(b) by 384 days.

(21) Appl. No.: 17/775,762

(22) PCT Filed: Dec. 8, 2020

(86) PCT No.: PCT/JP2020/045653
§ 371 (c)(1),
(2) Date: May 10, 2022

(87) PCT Pub. No.: WO2021/117716
PCT Pub. Date: Jun. 17, 2021

(65) Prior Publication Data
US 2023/0023990 A1  Jan. 26, 2023

(30) Foreign Application Priority Data
Dec. 9, 2019 (JP) ................. 2019-222254

(51) Int. Cl.
*A61F 13/496* (2006.01)
*A61F 13/49* (2006.01)
*A61F 13/15* (2006.01)

(52) U.S. Cl.
CPC ...... *A61F 13/496* (2013.01); *A61F 13/49011* (2013.01); *A61F 2013/1591* (2013.01)

(58) Field of Classification Search
CPC .............. A61F 13/496; A61F 13/49011; A61F 2013/1591; A61F 13/4963; A61F 13/475;
(Continued)

(56) References Cited

U.S. PATENT DOCUMENTS

| 6,676,647 B2 * | 1/2004 | Shimada ................. A61F 13/66 |
| | | 2/400 |
| 2005/0080394 A1 * | 4/2005 | Otsubo ............... A61F 13/5655 |
| | | 604/385.27 |

(Continued)

FOREIGN PATENT DOCUMENTS

| CN | 205094804 | 3/2016 |
| JP | 2002-035029 | 2/2002 |

(Continued)

OTHER PUBLICATIONS

International Search Report for PCT/JP2020/045653, dated Feb. 16, 2021.

*Primary Examiner* — Philip R Wiest
*Assistant Examiner* — Brandon W. Levy
(74) *Attorney, Agent, or Firm* — Andrus Intellectual Property Law, LLP

(57) ABSTRACT

An underpants-type disposable diaper wherein the end portions of elastic members are kept from being drawn in, and the bonding strength in side sealed portions is kept from deteriorating. The diaper has outer member defining front and back body sections, wherein side portions of the outer member in the front and back body sections are joined to form side sealed portions, which produce a waist opening and a pair of leg openings. The front and/or back body sections, are provided with a tortuous elastic member extending with curvature from one to the other of the side sealed portions, and bonded thereto with adhesive. The amount of adhesive applied to a zone neighbouring the inner zone of each side sealed portion is larger than that applied to the outer zone of each side sealed portion.

6 Claims, 11 Drawing Sheets

(58) Field of Classification Search
CPC .............. A61F 13/51394; A61F 13/535; A61F 13/5611; A61F 13/47; A61F 13/84; A61F 13/51496; A61F 13/472; A61F 13/4704; A61F 2013/49074; A61F 13/539
See application file for complete search history.

(56) References Cited

U.S. PATENT DOCUMENTS

| | | | |
|---|---|---|---|
| 2009/0005751 A1* | 1/2009 | Shirai | A61F 13/496 604/385.24 |
| 2009/0177176 A1* | 7/2009 | Saito | A61F 13/49019 604/385.29 |

FOREIGN PATENT DOCUMENTS

| | | |
|---|---|---|
| JP | 2002-035030 | 2/2002 |
| JP | 2002-178428 | 6/2002 |
| JP | 2002-273808 | 9/2002 |
| JP | 2012-139270 | 7/2012 |
| JP | 2013-123449 | 6/2013 |
| JP | 2013-202182 | 10/2013 |
| JP | 2017-192834 | 10/2017 |
| WO | 2013094591 | 6/2013 |

\* cited by examiner (10A)

(10B)

(11A)

(11B)

UNDERPANTS-TYPE DISPOSABLE DIAPER

CROSS-REFERENCE TO RELATED APPLICATIONS

This application is the U.S. national stage application of International Application PCT/JP2020/045653, filed Dec. 8, 2020, which international application was published on Jun. 17, 2021, as International Publication WO 2021/117716 in the Japanese language. The International Application claims priority of Japanese Patent Application No. 2019-222254, filed Dec. 9, 2019. The international application and Japanese application are both incorporated herein by reference, in entirety.

TECHNICAL FIELD

The present invention relates to underpants-type disposable diapers in which end portions of tortuous elastic members bonded to the outer member are kept from being drawn in.

BACKGROUND ART

An underpants-type disposable diaper includes an outer member defining a front body section and a back body section, and an inner member including an absorber body and fixed on the interior surface of the outer member. The front body section and the back body section are joined together along their opposed lateral sides to form side sealed portions, whereby a waist opening and a pair of right and left leg openings are defined.

When a wearer of an underpants-type disposable diaper excretes a large amount of urine, the absorber body absorbs the urine to increase its weight, causing sagging of the crotch portion of the diaper. This results in a gap formed between the skin of the wearer and the diaper, through which the urine may leak. In order to avoid worsening of fitting after urination by the wearer, diapers having tortuous elastic members arranged around the legs are manufactured and distributed. By pulling up the crotch portion of the diaper with such tortuous elastic members, leakage of urine is reduced.

In the production process of diapers, application of adhesive directly to the tortuous elastic members per se poses a risk. For example, the tortuous elastic members pass a positioning guide, which reciprocates in the direction orthogonal to the line direction, to thereby form the elastic members into the tortuous shape. Thus, if an adhesive is applied directly to the tortuous elastic members, there is a risk of the adhesive being scattered over the line as the positioning guide reciprocates. In view of this, for example, of the two fabric sheets which are being made into an outer member, an adhesive is applied to the top face of the lower sheet, the tortuous elastic members are disposed over the applied adhesive, the upper sheet is placed thereon, and the resulting upper and lower sheets having the tortuous elastic members interposed therebetween are then pressed between upper and lower rolls and hot-melted. The tortuous elastic members are bonded between the two sheets in this way, which sheets are cut in the transverse direction (in the direction orthogonal to the flow direction of the sheets) at predetermined intervals, to thereby give basic forms of a diaper. While the tortuous elastic members are also cut as the sheets are cut, the tortuous elastic members and the lower sheet, due to in general the tortuous elastic members having a small diameter, have small contact areas and thus not strong bonding therebetween, which poses a problem that the end portions of the tortuous elastic members are prone to be drawn inwards in the width direction of the diaper. If the tortuous elastic members are drawn inwards, contracting force is hard to act on both sides in the width direction of the diaper, which impairs fitting of the diaper on both sides in the width direction.

As a prior art publication relative to the present invention, Patent Publication 1 mentioned below may be referred to. This Patent Publication 1 discloses an absorbent article wherein leg region elastic members for forming leg gathers are arranged in the elongated state. The leg region elastic members are cut in the crotch region, so that elastic expansible/contractible property will not be exhibited in an area where the absorbent core exists. And a predetermined part of the leg region elastic members including a portion which does not exhibit elastic expansible/contractible property is fixed to the component of the absorbent article by second fixing means.

PRIOR ART PUBLICATION

Patent Publication
  Patent Publication 1: JP 2002-035030 A

SUMMARY OF THE INVENTION

Problems to be Solved by the Invention

For solving the problem mentioned above, it is conceivable to apply another adhesive to the end portions of the tortuous elastic members to increase the bonding strength of the tortuous elastic members. However, usually the end portions of the tortuous elastic members are located in the side sealed portions, so that the application of another adhesive to the end portions of the tortuous elastic members will increase the amount of adhesive applied to the side sealed portions. Bonding of the side sealed portions are often performed in a manner different from that of the elastic members mentioned above, for example, by ultrasonic bonding. In this case, with a large amount of adhesive applied between the two sheets, ultrasonic waves used in the ultrasonic bonding have difficulties in propagation, which tends to impair the bonding strength in the side sealed portions. It is also known that, in ultrasonic bonding to form the side sealed portions, the bonding strength of the sealed portions tends to be higher without any impurities between the upper and lower sheets. The adhesive for the tortuous elastic members is included in such impurities and, accordingly, for the purpose of increasing the bonding strength in the side sealed portions, the amount of the adhesive in the side sealed portions should be as little as possible. Further, a large amount of adhesive, if present in the side sealed portions, will bleed through the exterior surface of the sheets located in the side sealed portions, and may adhere to a conveyer or the like used in transferring the sheets in the production system. In addition, with a large amount of adhesive present in the side sealed portions, part of the sheets located in the side sealed portions may lose their flexibility, which may cause discomfort of the wearer when that part is in contact with his/her skin.

It is therefore a primary object of the present invention to provide an underpants-type disposable diaper in which the end portions of the elastic members are kept from being drawn in, and in which the bonding strength in the side sealed portions is kept from being impaired.

Means for Solving the Problem

The aspects of the present invention which solve these problems are as follows.

<First Aspect>

An underpants-type disposable diaper including an outer member defining a front body section and a back body section, wherein opposed lateral side portions of the outer member in the front body section are joined to opposed lateral side portions of the outer member in the back body section to form opposed lateral side sealed portions, which produce a waist opening and a pair of right and left leg openings, wherein at least one of the front body section and the back body section of the outer member is provided with a tortuous elastic member extending with curvature from one of the side sealed portions to the other of the side sealed portions, and bonded to the outer member with adhesive, and wherein an amount of adhesive applied to a zone neighboring an inner zone of each side sealed portion in a width direction is larger than an amount of adhesive applied to an outer zone of each side sealed portion in the width direction.

(Effect)

The underpants-type disposable diaper according to the first aspect is characterized in that the amount of adhesive applied to the zone neighboring the inner zone of each side sealed portion in the width direction is larger. In this neighboring zone, the end portions of the tortuous elastic members are located, and by increasing the amount of adhesive applied to the neighboring zone, the bonding between the end portions of the tortuous elastic members and the outer member is made firmer compared to that in the conventional diapers. As a result, drawing of the end portions of the tortuous elastic members inwards in the width direction of the diaper may be reduced compared to that in the conventional diapers.

Further, the underpants-type disposable diaper according to the first aspect is also characterized in that the amount of adhesive applied to the outer zone of each side sealed portion in the width direction is smaller. As discussed above, if a larger amount of adhesive is applied to the outer zone of each side sealed portion, the bonding strength in the side sealed portions is disadvantageously impaired. According to the present aspect, by making smaller the amount of adhesive applied to the outer zone of each side sealed portion in the width direction, the degradation of the bonding strength in the side sealed portions is reduced. At the same time, leakage of the adhesive through the outer edge of each side sealed portion in the width direction may also be reduced. Further, bleeding of the adhesive through the exterior surface of the side sealed portions, and resulting hardening thereof, as well as discomfort of the wearer felt in touching the hardened portion, may also be reduced.

<Second Aspect>

The underpants-type disposable diaper according to the first aspect, wherein the amount of adhesive applied to the neighboring zone is larger than an amount of adhesive applied to the side sealed portion.

(Effect)

The underpants-type disposable diaper according to the second aspect is characterized in that the amount of adhesive applied to the entire side sealed portions is smaller. With the smaller amount of adhesive applied to the entire side sealed portions, degradation of the bonding strength in the side sealed portions may further be reduced, compared to the side sealed portions having a zone to which a larger amount of adhesive is applied. In addition, probability of the adhesive bleeding through the exterior surface of the side sealed portions may further be reduced, which further reduces the chance of the wearer feeling discomfort as discussed above.

<Third Aspect>

The underpants-type disposable diaper according to the first aspect, wherein an amount of adhesive applied to the inner zone of the side sealed portion in the width direction and to the neighboring zone is larger than the amount of adhesive applied to the outer zone of the side sealed portion in the width direction.

(Effect)

In the manufacture of diapers, it is not easy to precisely adjust the amount of adhesive applied to each zone of a diaper, such as making larger the amount of adhesive applied to the neighboring zones while making smaller the amount of adhesive applied to the entire side sealed portions. This is because, in the manufacturing scene, a ribbon-like sheet, which is to be made into the outer members, is transferred at high speed, and it is thus generally hard to intermittently change the amount of adhesive applied to the sheet being transferred at high speed, and to apply strictly different amounts of adhesive on each side of the border area between the neighboring zone and the side sealed portion.

Thus, according to the third aspect, the amount of adhesive applied not only to the neighboring zone, but also to the inner zone of the side sealed portion in the width direction is made larger. As the inner zone of the side sealed portion in the width direction has a certain span in the width direction, control of the application zones may be easier, compared to the differentiation of the amounts of adhesive applied on each side of the border area between the side sealed portion and the neighboring zone. In addition, the amount of adhesive applied to the outer zone of the side sealed portion in the width direction remains small, so that the leakage of the adhesive through the outer edge of the side sealed portion in the width direction may also be reduced.

<Fourth Aspect>

The underpants-type disposable diaper according to any one of the first to third aspects, wherein the tortuous elastic member is not present in the outer zone of the side sealed portion in the width direction.

(Effect)

The underpants-type disposable diaper according to the fourth aspect is characterized in that the tortuous elastic member is not present in the outer zone of the side sealed portion in the width direction. If a tortuous elastic member is present in the outer zone of the side sealed portion in the width direction, irregularities derived from the tortuous elastic member are produced in the outer zone of the side sealed portion in the width direction, where gaps are formed between the exterior surface of the tortuous elastic member and the outer member and, through the gaps, the adhesive may easily pass and seep through the outer edge of each side sealed portion in the width direction. According to this aspect, for preventing such seepage of the adhesive, the tortuous elastic member is eliminated from the outer zone of the side sealed portion in the width direction.

Effect of the Invention

As discussed above, according to the present invention, underpants-type disposable diapers are provided in which the end portions of the elastic members are kept from being drawn in, and in which the bonding strength in the side sealed portions is kept from deteriorating.

BRIEF DESCRIPTION OF THE DRAWINGS

FIG. 10 shows enlarged views of area M in FIG. 9, wherein FIG. 10A and FIG. 10B illustrate different embodiments with different zones in which a smaller amount of the adhesive is applied.

FIG. 11 shows variations of FIG. 10, wherein FIGS. 11A and 11B illustrate different embodiments with different zones in which a larger amount of adhesive is applied.

EMBODIMENTS FOR CARRYING OUT THE INVENTION

Figure 1:
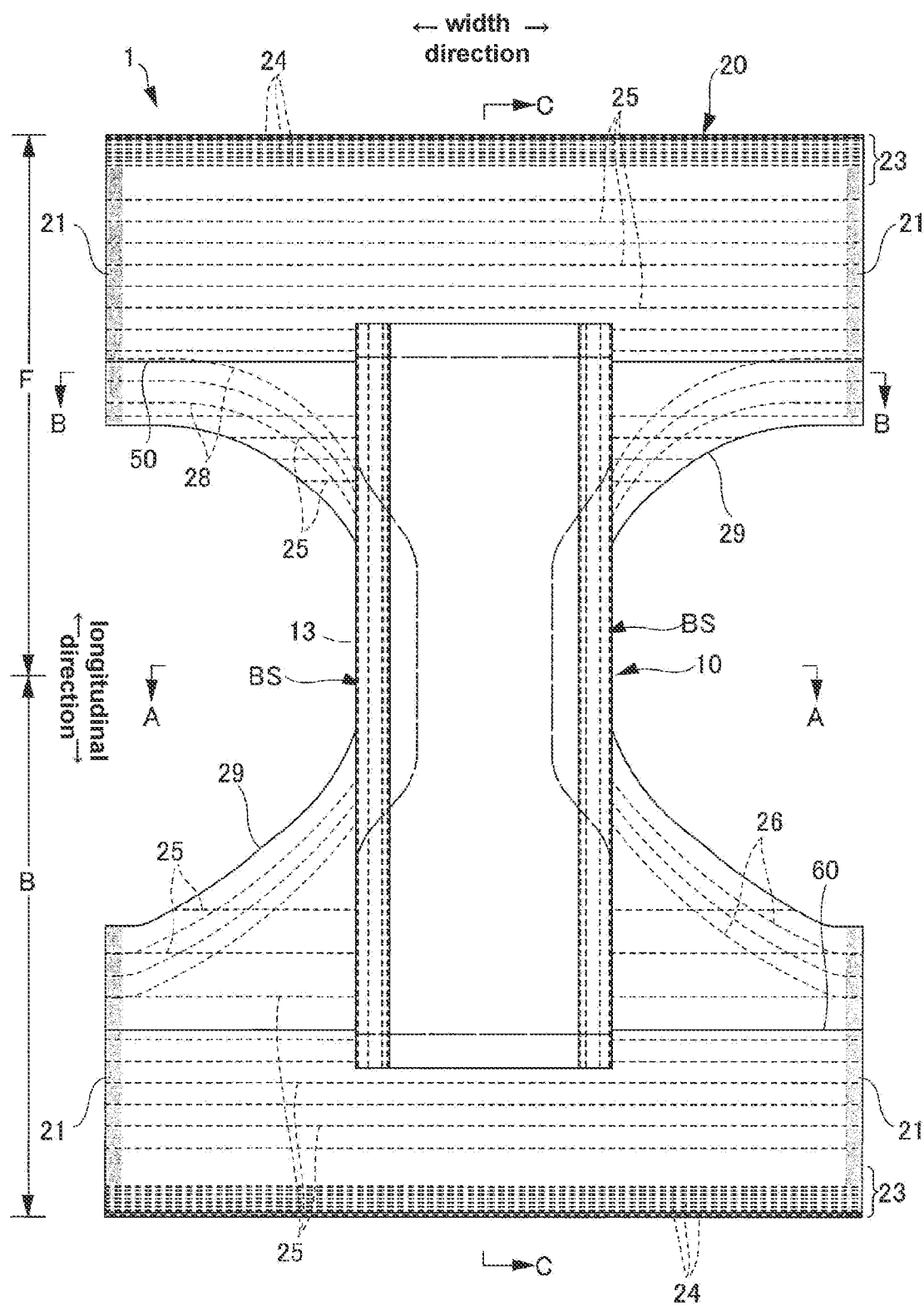
FIG. 1 is a plan view of an underpants-type disposable diaper in its spread state, illustrating the interior surface thereof.

An embodiment of the present invention will now be explained in detail with reference to the attached drawings. Note that the term "stretch rate" refers to a value with respect to the natural length being 100%.

FIGS. 1 to 6 show an underpants-type disposable diaper 1 according to an embodiment. This underpants-type disposable diaper 1 (referred to simply as the diaper hereinbelow) has an outer member 20 defining a front body section F and a back body section B, and an inner member 10 integrally fixed on the interior surface of the outer member 20. The inner member 10 is composed of a liquid-pervious top sheet 11, a liquid-impervious underside sheet 12, and an absorber body 13 interposed therebetween. In production, the under face of the inner member 10 is fixed to the interior surface (top face) of the outer member 20 with joining means, such as a hot melt adhesive G, then the inner member 10 and the outer member 20 together are folded along the lateral line passing the longitudinal (front-back direction) center and forming a border between the front body section F and the back body section B, and the opposed lateral side portions in the front body section and the opposed lateral side portions in the back body section are joined together by means of ultrasonic bonding or the like (thermal melt-bonding or a hot melt adhesive may alternatively be employed) to form opposed side sealed portions 21, resulting in an underpants-type disposable diaper having a waist opening and a pair of right and left leg openings defined therein.

Example of Outer Member Structure

Figure 3:
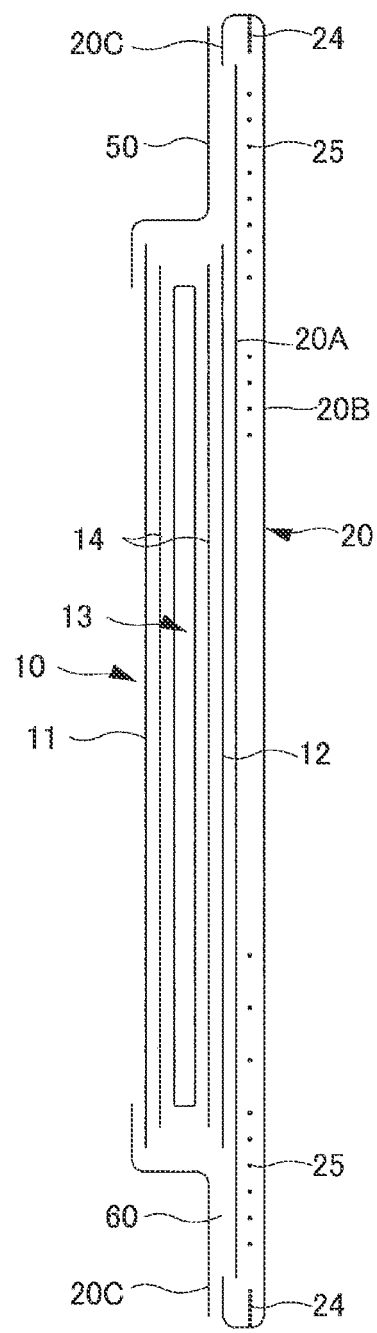
FIG. 3 is a sectional view taken along lines C-C in FIG. 1.
Figure 4:
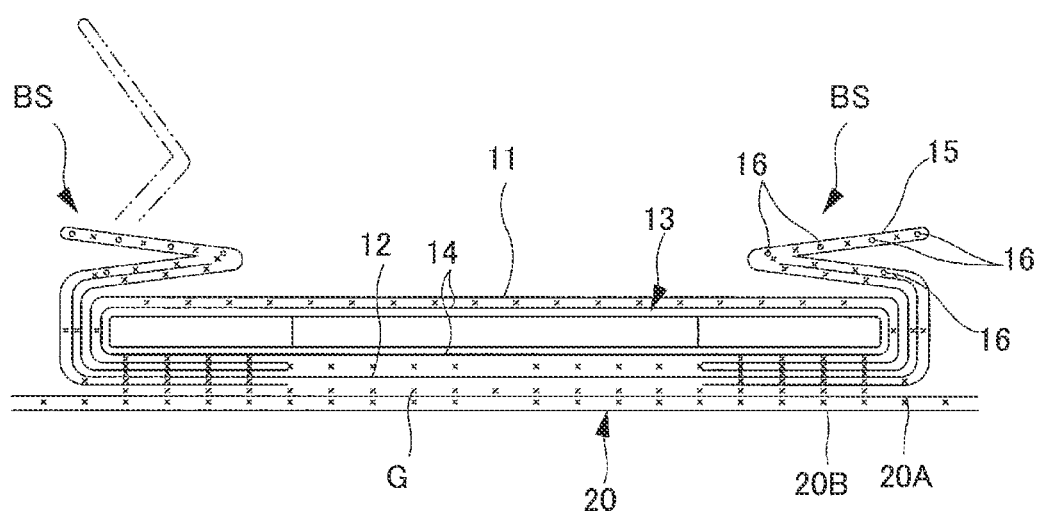
FIG. 4 is a cross sectional view taken along lines A-A in FIG. 1.
Figure 5:
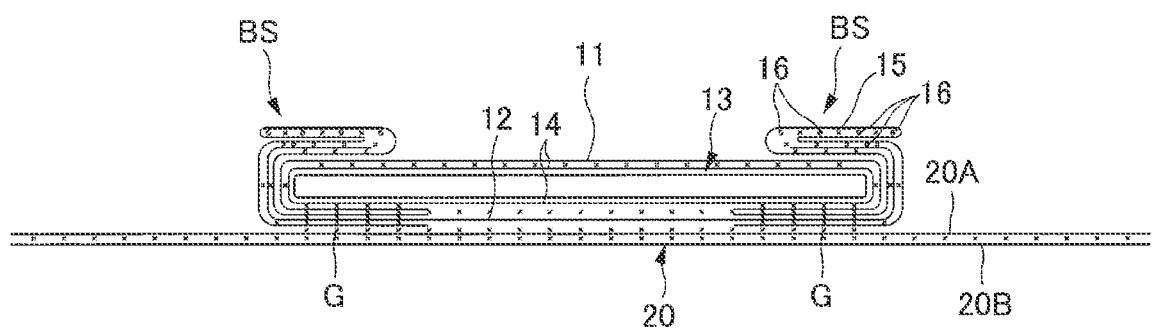
FIG. 5 is a cross sectional view taken along lines B-B in FIG. 1.

The outer member 20 is, as shown in FIGS. 3 to 5, a two-layered nonwoven sheet composed of upper nonwoven fabric 20A and lower nonwoven fabric 20B (i.e., in this embodiment, the lower nonwoven fabric is the outermost nonwoven fabric). Between the upper nonwoven fabric 20A and the lower nonwoven fabric 20B, as well as between the doubled nonwoven fabric in the folded portion 20C formed by folding the lower nonwoven fabric 20B back onto the interior surface side along the waist opening edge, various elastic members are disposed to impart elasticity. The plan shape is, as a hole, like an hourglass contoured with a centrally-curved round-leg line 29 formed in the middle on each lateral side for forming a leg opening.

Figure 2:
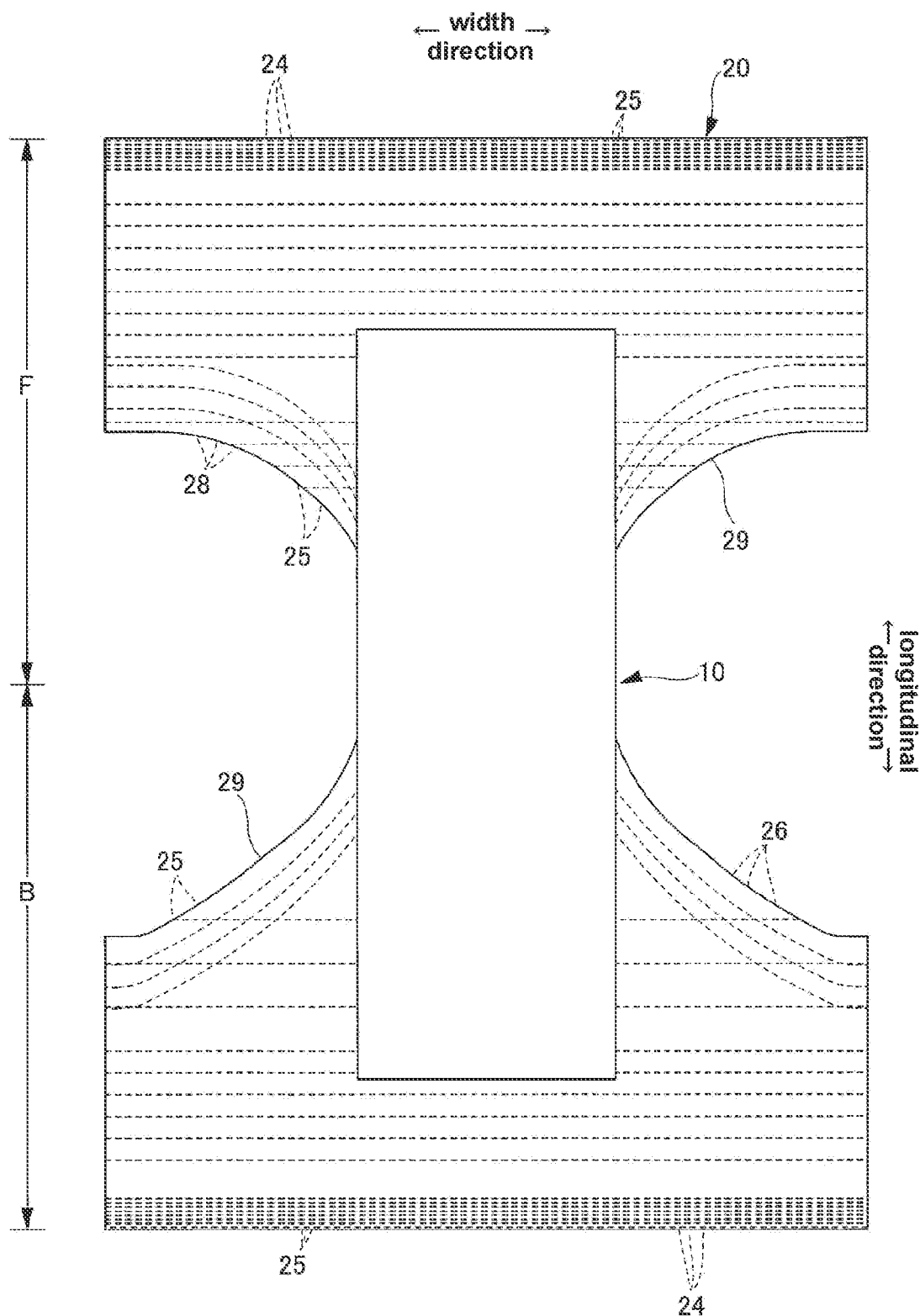
FIG. 2 is a plan view of the underpants-type disposable diaper in its spread state, illustrating the exterior surface thereof.

In particular, the outer member 20 of the illustrated embodiment has the elastic members, which are, as seen in the spread state as shown in FIGS. 1 and 2, waist zone elastic members 24 arranged in the vicinity 23 of the waist opening, a plurality of hip elastic members 25 arranged in the front body section F and the back body section B and extending in the width direction at longitudinal intervals and, in each of the front body section F and the back body section B, separately from a group of the hip elastic members, a plurality of tortuous elastic members 26, 28 arranged at intervals without intersection, each extending in a curved manner from one 21 of the opposed side sealed portions along one of the leg openings, across the crotch portion, further along the other of the leg openings up to the other 21 of the side sealed portions. Each of these elastic members 24 to 26 and 28 is fixed in its stretched state at a predetermined stretch rate along the respective direction of extension. Note that in the present outer member 20, so-called round-leg elastic members are not provided, each extending from the side sealed portion in the front body section F along the round-leg line 29 up to the side sealed portion in the back body section B.

The waist zone elastic members 24 are in the form of a plurality of threads of elongate elastic members, such as rubber threads, arranged at vertical intervals in the vicinity of the waist opening edge within the extension of the side sealed portions joining the front body section F and the back body section B, and produce stretching/contracting force to constrict around the body in the waist zone for fitting the diaper. The waist zone elastic members 24, which are rubber threads in the illustrated embodiment, may be, for example, a stretchable member in the form of a tape. Further, the waist zone elastic members 24, which are held in the folded portion 20C of the lower nonwoven fabric 20B between the doubled nonwoven fabric in the waist zone in the illustrated embodiment, may be held between the upper nonwoven fabric 20A and the lower nonwoven fabric 20B.

The hip elastic members 25 are in the form of elongate elastic members, such as rubber threads, arranged at vertical intervals generally from the upper side over to the lower side within the extent of the side sealed portions 21, and produce stretching/contracting force in the width direction in the hip regions of the front body section F and the back body section B to bring the diaper into close contact with the body. The west region elastic members 24 and the hip elastic members 25 may not necessarily be clearly divided along a boundary. For example, it suffices that, among the elastic members arranged at vertical intervals, each extending in the width direction, in the front body section F and in the back body section B, some from the upper side, though the number may not be specified, function as the waist zone elastic members, while the remaining elastic members function as the hip elastic members.

In the back body section B, dorsal tortuous elastic members 26 provided separately from the hip elastic members 25 are in the form of elongate elastic members, such as rubber threads. Only one dorsal tortuous elastic member 26 may be provided, but preferably a plurality of them is provided as in the illustrated embodiment, wherein three elastic members in the form of rubber threads are provided. These dorsal tortuous elastic members 26 are arranged at intervals without intersection. Such a group of dorsal tortuous elastic members 26 is not provided substantially as a bunch of about two or three elastically stretchable members arranged at close intervals, but preferably three or more dorsal tortuous elastic members 26 are arranged at intervals of 3 to 20 mm, preferably about 6 to 16 mm, to form a predetermined stretchable zone.

In the front body section F of the outer member 20, ventral tortuous elastic members 28 provided separately from the hip elastic members 25 are in the form of elongate elastic members, such as rubber threads. Only one ventral tortuous elastic member 28 may be provided, but preferably a plurality of them is provided as in the illustrated embodiment, wherein three elastic members in the form of rubber threads are provided. These ventral tortuous elastic members 28 are arranged at intervals without intersection. Such a group of ventral tortuous elastic members 28 is not provided substantially as a bunch of about two to three elastically stretchable members arranged at close intervals, but preferably three or more ventral tortuous elastic members 28 are arranged at intervals of 3 to 20 mm, preferably about 6 to 16 mm, to form a predetermined stretchable zone.

Figure 7:
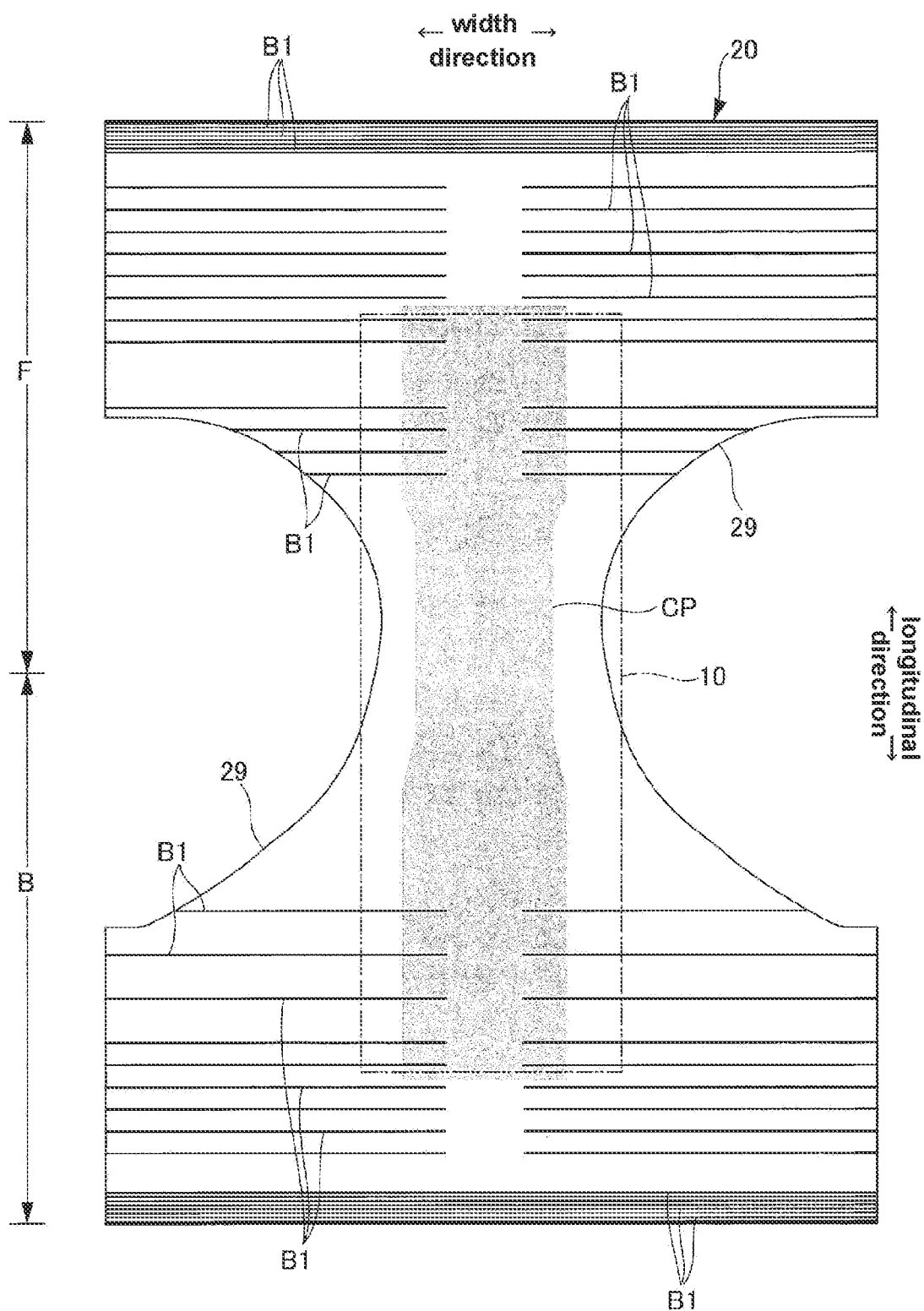
FIG. 7 is a plan view illustrating an example of an application pattern of the adhesive for bonding the waist zone elastic members and the hip elastic members.
Figure 8:
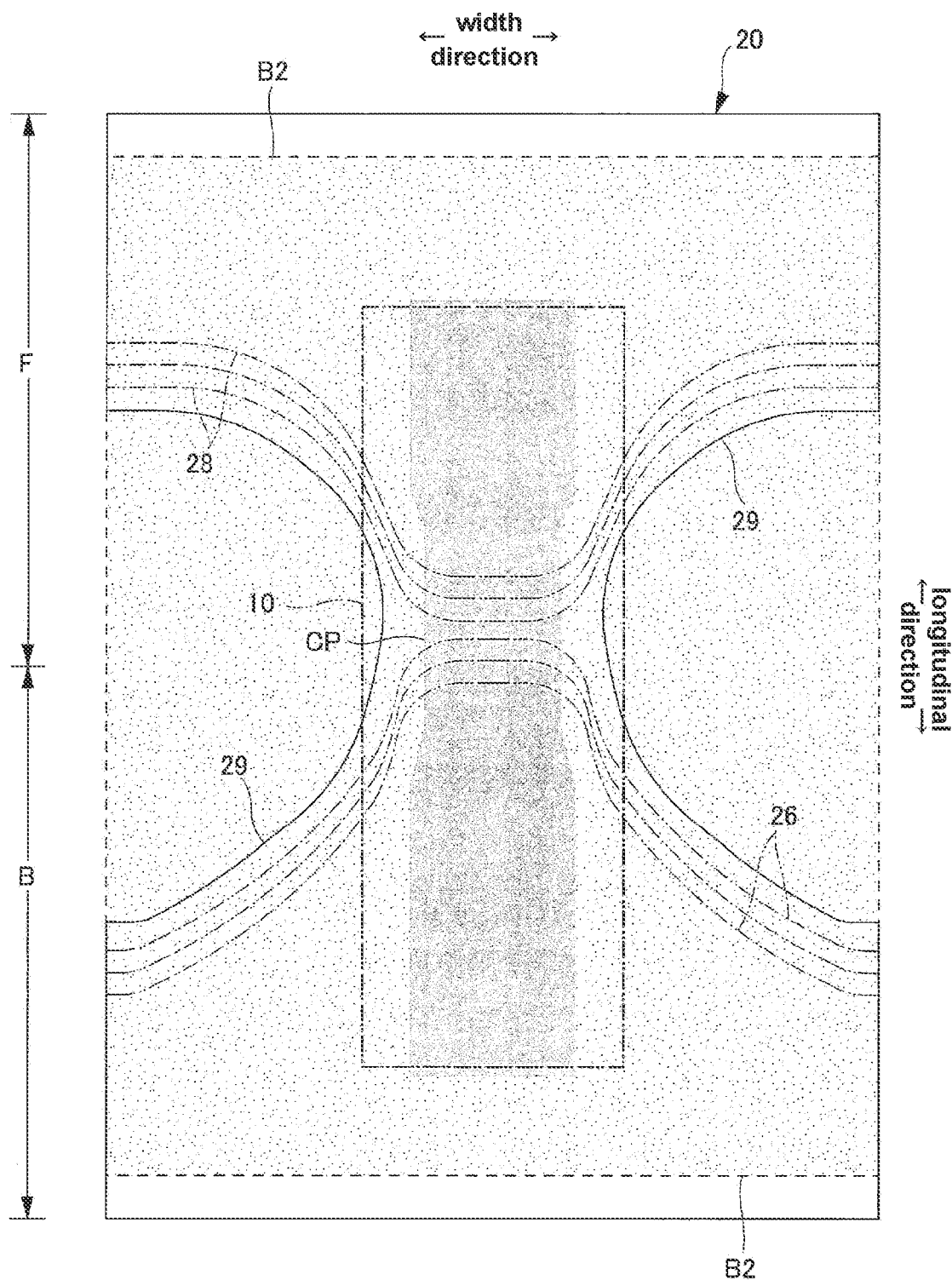
FIG. 8 is a plan view illustrating an application pattern of the adhesive for bonding the tortuous elastic members and the hip elastic members.

Note that, in the illustrated embodiment, during manufacture, each of the hip elastic members 25 and the tortuous elastic members 26, 28 arranged in the front body section F and in the back body section B is unintermittently fixed to the outer member as shown in FIGS. 7 and 8, and then part or all of a portion of the elastic members 25, 26, 28 that overlaps the inner member is finely cut in a predetermined cutting pattern CP to provide a non-contractible region wherein the contraction force does not act (i.e., the region overlapping the cutting pattern CP in FIGS. 7 and 8), whereas the portions of the elastic members 25, 26, 28 extending laterally from the non-contractible region in a curved manner provide contractible regions wherein the contraction force acts (i.e., the regions having the hip elastic members 25 and the tortuous elastic members 26, 28 remaining unintermittently, and positioned laterally to the cutting pattern CP in FIGS. 7 and 8). In this way, the hip elastic members 25 and the tortuous elastic members 26, 28 are disposed unintermittently from one of the side sealed portions 21 across the inner member 10 up to the other (on the opposed side) of the side sealed portions 21, and then part or all of the portion of each elastic member that overlaps the inner member is finely cut. This further assists avoiding contraction of the inner member (in particular, the absorber body 13) in the width direction. Needless to say, the hip elastic members 25 and the tortuous elastic members 26, 28 may be disposed unintermittently across the inner member 10.

The outer member 20 discussed above may be manufactured using the technologies disclosed, for example, in JP H04-28363 A or JP H11-332913 A. The tortuous elastic members 26, 28 may be cut on the inner member 10 into an intermittent state preferably using the cutting method disclosed in JP 2002-035029 A, JP 2002-178428 A, or JP 2002-273808 A.

Unlike the illustrated embodiment, tortuous elastic members may be provided in only either one of the front body section F and the back body section B. When the tortuous elastic members 26, 28 are provided in both the front body section F and in the back body section B, an embodiment (not shown) may be conceivable in which part or all of a group of tortuous elastic members arranged on the front body section F side intersects with part or all of a group of tortuous elastic members arranged on the back body section B side, but the embodiment as illustrated is preferred, in which the group of tortuous elastic members 28 arranged on the front body section F side and the group of tortuous elastic members 26 arranged on the back body section B side do not intersect with each other, and are arranged longitudinally spaced apart from each other in the middle of the front-back direction, in particular, at a position slightly closer to the front body section F.

Further, each of the tortuous elastic members 26, 28 may not be curved all through the member and may partially have straight portions.

The stretch rates of the elastic members 24-26, 28 in the fixed states may suitably be decided. For ordinary baby diapers, the stretch rate of the waist zone elastic members 24 may be about 230 to 320%, that of the hip elastic members 25 may be about 230 to 320%, and that of the tortuous elastic members 26, 28 may be about 160 to 300%.

<Fixing of Elastic Members with Hot Melt Adhesive>

The waist zone elastic members 24, the hip elastic members 25, and the tortuous elastic members 26, 28 are held and adhesively fixed with a hot melt adhesive between a pair of sheet layers 20A, 20B constituting the outer member 20, and the amount of the hot melt adhesive applied significantly affects the flexibility of the outer member 20. Accordingly, as shown in FIG. 7, it is preferred that areas B1 where adhesive is applied for fixing the waist zone elastic members 24 and the hip elastic members 25 are preferably limited to only the areas where the waist zone elastic members 24 are located and in the vicinity thereof and the areas where the hip elastic members 25 are located and in the vicinity thereof.

FIG. 7 illustrates the areas B1 where a hot melt adhesive is applied during the manufacturing process, and the hot melt adhesive for fixing the waist zone elastic members 24 and the hip elastic members 25 between the two sheet layers 20A, 20B is applied substantially only to the areas where the elastic members 24, 25 are located and in the vicinity thereof. Such application of the adhesive may be realized by interposing between the two sheet layers 20A, 20B the elastic members 24, 25 having the adhesive applied on their exterior surface, and such application of the adhesive on the exterior surface of the elastic members 24, 25 may be carried out, for example, using SureWrap (trademark) nozzles manufactured by Nordson Corporation.

FIG. 8 illustrates area B2 where a hot melt adhesive is applied during the manufacturing process, wherein the tortuous elastic members 26, 28 are shown in chain double-dashed lines in the state before the portions crossing the inner member 10 are finely cut. Note that, in FIG. 8, for ready conception of the drawings, illustration of the waist zone elastic members 24 and the hip elastic members 25 is eliminated for the sake of convenience. As shown in FIG. 8, the hot melt adhesive is also applied to almost the entire surface (location of the application area B2) of a disposable diaper. This is used not only for bonding between the upper nonwoven fabric layer 20A and the lower nonwoven fabric layer 20B, but also for bonding of the hip elastic members 25 and the tortuous elastic members 26, 28. Note that, in the manufacture of diapers, the upper nonwoven fabric layer 20A and the lower nonwoven fabric layer 20B are in the form of fabric sheets in the initial process, and the nonwoven fabric is present also in the area inside each round-leg line 29 (the area in which each leg of the wearer is to be inserted), which area the adhesive is also applied to, but is to be cut out in the subsequent process. In general, the adhesive illustrated in FIG. 8 is applied to either one of the upper nonwoven fabric layer 20A and the lower nonwoven fabric layer 20B.

Discussion has hitherto been made about application of adhesive to both the application areas B1 and B2 in the manufacture of diapers as shown in FIGS. 7 and 8. The present invention is characterized in that, in the application of adhesive, the amount of adhesive applied to a zone N1 neighboring the inner zone of each side sealed portion 21 in the width direction is larger than the amount of adhesive applied to the outer zone N2 of each side sealed portion 21 in the width direction, as shown in FIG. 10A.

Figure 9:
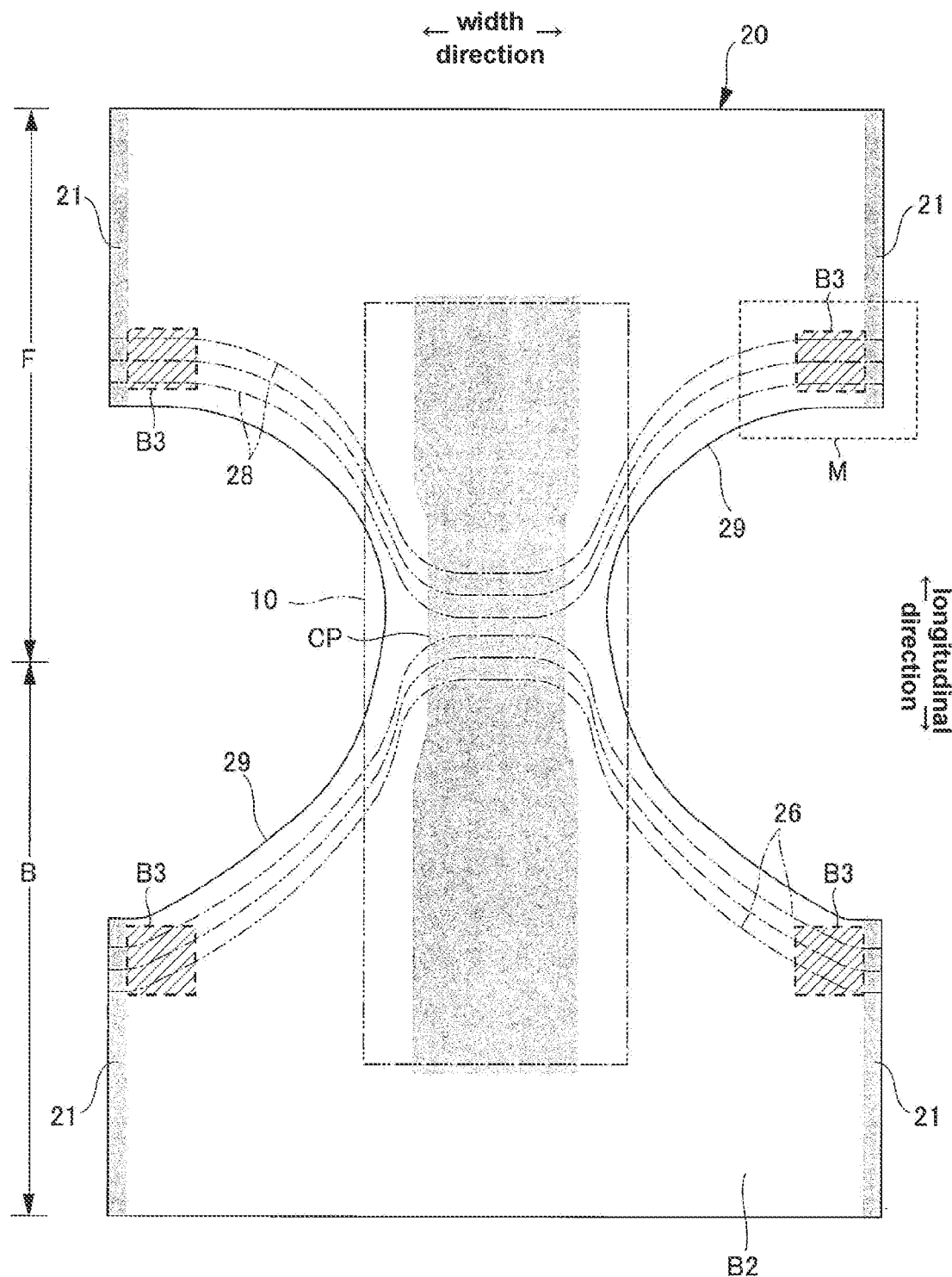
FIG. 9 is a plan view illustrating the zones in which a larger amount of adhesive for bonding the tortuous elastic members is applied, while indication of the zones in which a smaller amount of adhesive is applied is omitted.
Figure 10:
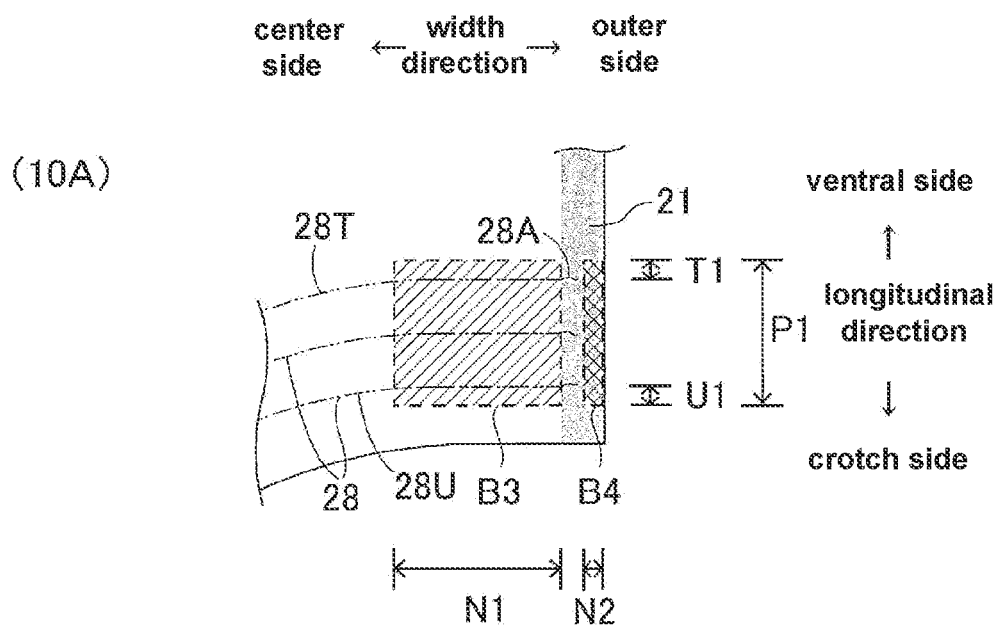
Figure 10:
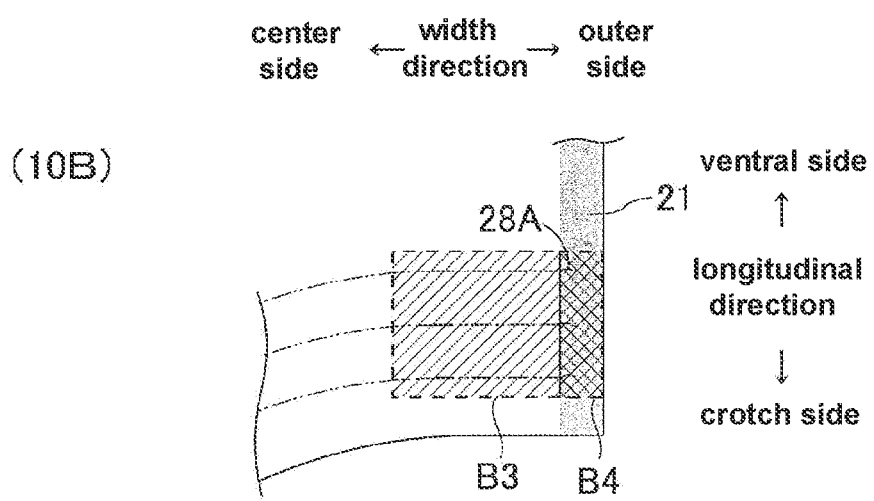
Figure 11:
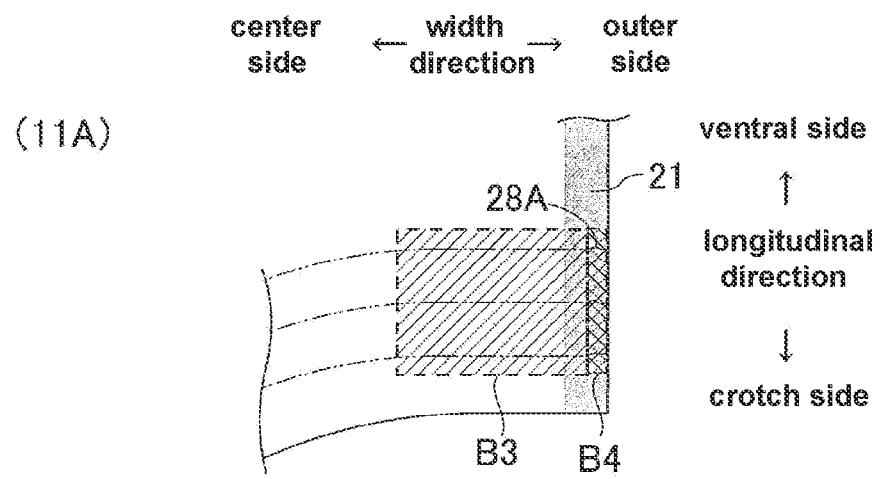
Figure 11:
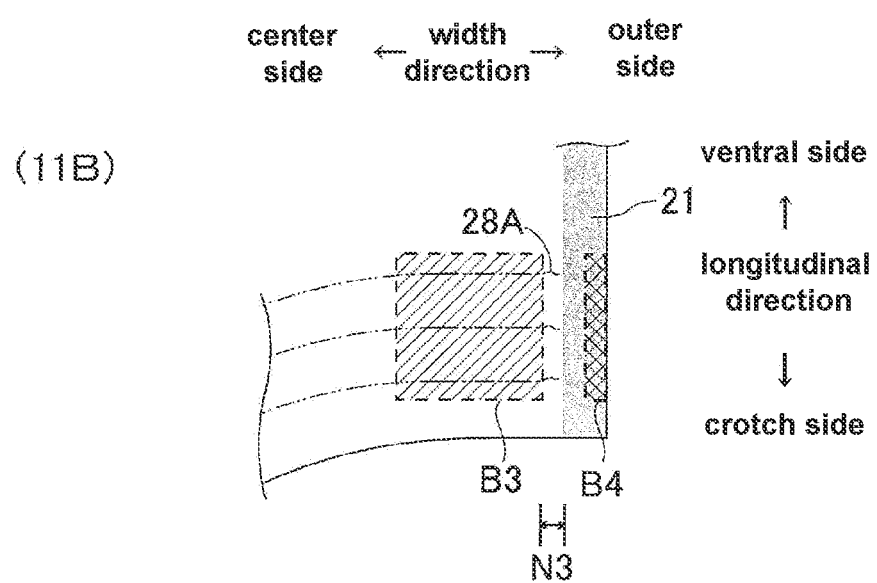

FIG. 9 illustrates that an adhesive in addition to the ones applied in FIGS. 7 and 8 is applied to the zone N1 neighboring the inner zone of each side sealed portion 21. The area where this adhesive is applied is depicted as application area B3. By applying the additional adhesive, the amount of adhesive applied to the neighboring zone N1 may be multiplied. As a result, the neighboring zone N1 has a larger amount of adhesive applied thereto, compared to the remaining zone where this adhesive is not applied (in particular, the outer zone N2 of each side sealed portion 21 in the width direction). With the larger amount of adhesive applied to the neighboring zone N1, the end portions of the tortuous elastic members 26, 28 are firmly bonded to the upper nonwoven fabric layer 20A and the lower nonwoven fabric layer 20B, which keeps the end portions of the tortuous elastic members 26, 28 from being drawn in. FIGS. 10 and 11 illustrate that firm bonding of the end portions of the ventral tortuous elastic members 28 resulted in smaller portions 28A of the ventral tortuous elastic members 28 that have been drawn in. In addition, with the smaller amount of adhesive applied to the outer zone N2 of each side sealed portion 21 in the width direction, leakage of the adhesive through the outer edge of each side sealed portion 21 in the width direction may be avoided. Further, as discussed above, there is a problem that a larger amount of adhesive applied to the side sealed portions 21 proportionally lowers the bonding strength in the side sealed portions 21. The reduction in the amount of adhesive applied to the outer zone N2 of each side sealed portion 21 in the width direction keeps the bonding strength in the side sealed portions 21 from deteriorating.

FIG. 10A illustrates that an area B4 where a smaller amount of adhesive is applied is provided only in the outer zone N2 of each side sealed portion 21 in the width direction. More preferably, however, as shown in FIG. 10B, the area B4 where a smaller amount of adhesive is applied is provided also in the inner zone of each side sealed portion 21 in the width direction. This is because the smaller the amount of adhesive applied to each side sealed portion 21, the more the lowering in bonding strength may be reduced. In addition, the smaller the amount of adhesive applied to each side sealed portion 21, the more the bleeding of the adhesive through the exterior surface of the side sealed portion 21 and the resulting hardening of the adhesive thereon, and thus discomfort of the wearer felt in touching the hardened portion, may be reduced.

FIG. 11 shows another embodiment. FIG. 11A illustrates an embodiment in which the area B3 where a larger amount of adhesive is applied is provided not only in the neighboring zone N1, but also in the inner zone of each side sealed portion 21 in the width direction. This embodiment illustrated in FIG. 11A is not preferred in terms of the fact that a larger amount of adhesive applied to each side sealed portion 21 proportionally lowers the bonding strength in the side sealed portion 21. However, in the manufacturing process, the upper nonwoven fabric 20A and the lower nonwoven fabric 20B are transferred at high speed, so that it is hard to apply adhesive intermittently only in the predetermined zone (neighboring zone N1) of the upper nonwoven fabric 20A and the lower nonwoven fabric 20B. Thus, application to a zone slightly outwards of the neighboring zone N1 in the width direction is permissible.

FIG. 11B illustrates an embodiment in which the area B3 where a larger amount of adhesive is applied is not present on the outside of the neighboring zone N1 in the width direction (zone N3). In this embodiment, the portions 28A of the ventral tortuous elastic members 28 that have been drawn in do not overlap the side sealed portion 21. If the ventral tortuous elastic members 28 are present in the side sealed portions 21, irregularities derived from the ventral tortuous elastic members 28 in the side sealed portions 21 are produced, where gaps are formed between the exterior surface of the ventral tortuous elastic members 28 and the outer member and, through the gaps, the adhesive may easily pass and seep through the outer edge of each side sealed portion 21 in the width direction. In this embodiment, as the portions 28A of the ventral torturous elastic members 28 that have been drawn in do not overlap the side sealed portion 21, such seepage of the adhesive may be avoided. Note that also in the embodiments shown in FIGS. 10A and 10B, the portions 28A of the ventral tortuous elastic members 28 that have been drawn in are not present in the outer zone N2 of each side sealed portion 21. This is because the amount of the adhesive applied to the outer zone N2 of the side sealed portion 21 in the width direction is smaller. In this way, in the outer zone N2 of each side sealed portion 21 in the width direction, there is little risk that irregularities derived from the ventral tortuous elastic members 28 are produced, where gaps are formed between the exterior surface of the ventral tortuous elastic members 28 and the outer member and, through the gaps, the adhesive may easily pass and seep through the outer edge of each side sealed portion 21 in the width direction.

So far, the embodiments have been discussed in which the adhesive in addition to the ones applied in FIGS. 7 and 8 is applied in order to form the areas B3 where a larger amount of adhesive is applied, but the present invention is not limited to such embodiments. For example, regarding the adhesive to be applied to the application area B2 as shown in FIG. 2, a larger amount of this adhesive may be applied to the zones corresponding to the neighboring zones N1, compared to the amount to be applied to the remaining zone, to thereby form the areas B3 where a larger amount of adhesive is applied.

Note that, in the discussion of the present embodiments, the outer zone of a side sealed portion 21 in the width direction refers to, dividing the width of a side sealed portion into approximate halves, the half which is located on the outer side in the width direction, whereas the inner zone of a side sealed portion 21 in the width direction refers to, dividing the width of a side sealed portion into approximate halves, the half which is located on the inner side in the width direction. The above-mentioned neighboring zone N1 refers to the zone starting from the inner border of a side sealed portion 21 in the width direction, and extending inwards within the extension of 5 to 60 mm in the width direction.

The amount of adhesive applied to the areas B3 where a larger amount of adhesive is applied is about 11 to 25 g/m$^2$, whereas the amount of adhesive applied to the areas B4 where a smaller amount of adhesive is applied is about 1 to 5 g/m². The amount of adhesive applied to the areas B3 where a larger amount of adhesive is applied is about 2 to 25 times the amount of adhesive applied to the areas B4 where a smaller amount of adhesive is applied.

In FIG. 9, the areas B3 where a larger amount of adhesive is applied are provided both for the ventral tortuous elastic members 28 in the front body section F and for the dorsal elastic members 28 in the back body section B, but may be provided only for either one of them. Further, it suffices that the areas B3 where a larger amount of adhesive is applied and the areas B4 where a smaller amount of adhesive is applied are provided only in the regions where the ventral tortuous elastic members 28 or the dorsal tortuous elastic members 26 are present. That is, the areas B3 and B4 are not necessarily provided in a region longitudinally far from the ventral tortuous elastic members 28 or the dorsal tortuous elastic members 26. Specifically, it suffices that the areas B3 and B4 may be provided within a range longitudinally spaced 0.5 to 10 mm from the ventral tortuous elastic members 28 or the dorsal tortuous elastic members 26. For example, in the embodiment shown in FIG. 10A, three ventral tortuous elastic members 28 are arranged in approximate parallel at certain longitudinal intervals. Here, the position upwardly (ventrally) spaced 0.5 to 10 mm (i.e., T1 is 0.5 to 10 mm) from the upper edge of the ventral torturous elastic member 28T located most ventrally (corresponding to the exterior surface of the ventral tortuous elastic member 28 in FIG. 10A) may be the upper boundary of the area B3 where a larger amount of adhesive is applied. Similarly, the position downwardly (toward the crotch) spaced 0.5 to 10 mm (i.e., U1 is 0.5 to 10 mm) from the upper edge of the ventral tortuous elastic member 28 U located closest to the crotch section (corresponding to the exterior surface of the ventral tortuous elastic member 28 in FIG. 10A) may be the lower boundary of the area B3 where a larger amount of adhesive is applied. In the light of readiness of production or the like, it is preferred to make the entire area between the ventral tortuous elastic member 28T located most ventrally and the ventral tortuous elastic member 28U located closest to the crotch section, to be the area B3 where a larger amount of adhesive is applied. Accordingly, with three ventral tortuous elastic members 28, the longitudinal dimension P1 of the area B3 where a larger amount of adhesive is applied is preferably about 15 to 50 mm.

In the above, discussion has been made about the area B3 where a larger amount of adhesive is applied, provided around the ventral tortuous elastic members 28, and the similar value is applicable to the area B3 where a larger amount of adhesive is applied, provided around the dorsal tortuous elastic members 26. Further, the longitudinal extension of the area B4 where a smaller amount of adhesive is applied may be regarded as the same as the longitudinal extension of the area B3 where a larger amount of adhesive is applied.

For providing the area B3 where a larger amount of adhesive is applied, when a reinforcing adhesive (a reinforcing adhesive for keeping the end portions of the tortuous elastic members 26, 28 from being drawn in) in addition to the one for the solid application as shown in FIG. 8 is used, the reinforcing adhesive may be applied to the sheet (e.g., the upper nonwoven fabric 20A) different from the one to which the adhesive for the solid application is applied (e.g., the lower nonwoven fabric 20B). Note that the adhesive for the solid application is the basic adhesive which is used in bonding the upper nonwoven fabric 20A and the lower nonwoven fabric 20B as well as the tortuous elastic members 26, 28 interposed therebetween, whereas the reinforcing adhesive is for keeping the end portions of the tortuous elastic members 26, 28 from being drawn in. The adhesive for the solid application and the reinforcing adhesive may be of the same or different types. The adhesive for the solid application and the reinforcing adhesive are not particularly limited, and may be, for example, a hot melt adhesive. This hot melt adhesive is not particularly limited, and may be, for example, EVA, pressure-sensitive rubber (elastomeric), polyolefin, or polyester-polyamide adhesive.

Example of Inner Member Structure

Figure 6:
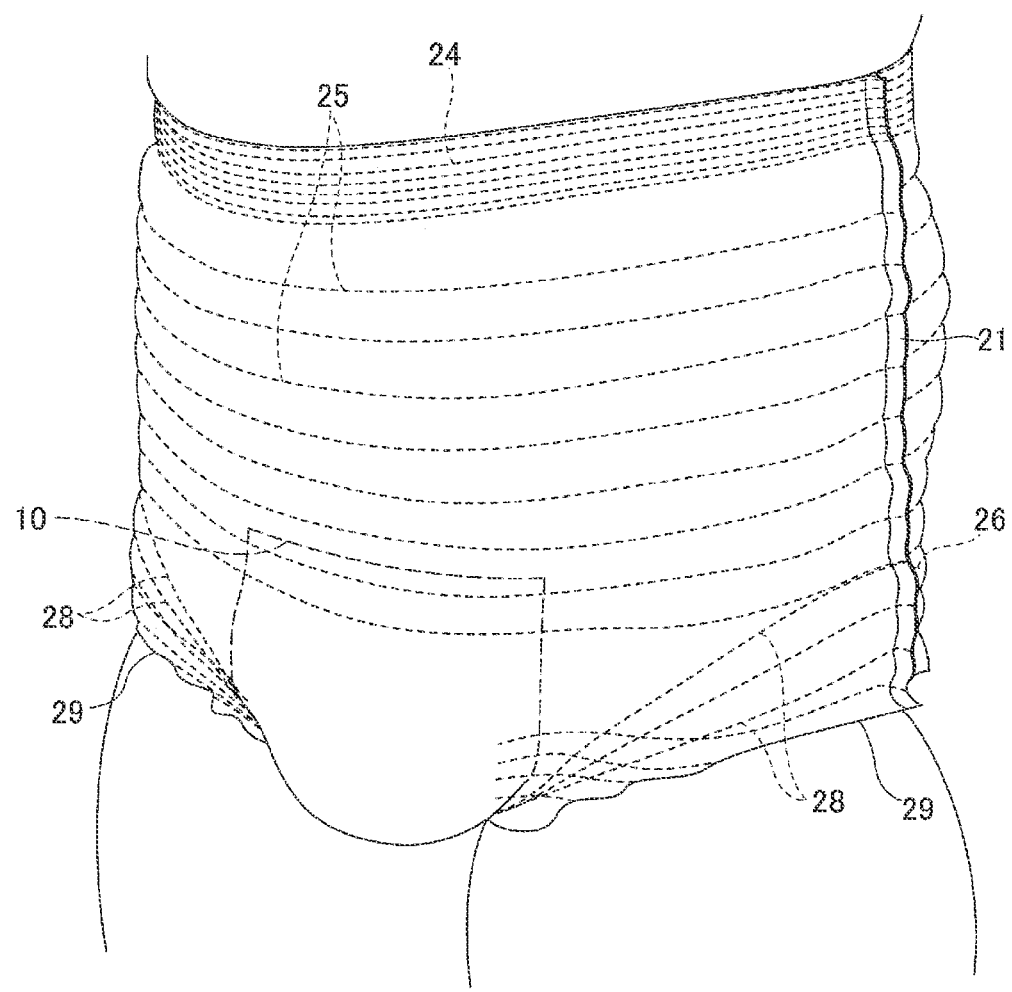
FIG. 6 is a perspective view of the underpants-type disposable diaper in a worn state.

The inner member 10 has a structure having, as shown in FIGS. 4 to 6, a liquid-pervious top sheet 11 formed of nonwoven fabric or the like, a liquid-impervious underside sheet 12 made of polyethylene or the like, and an absorber body 13 interposed therebetween, and absorbs and holds excreted liquid permeated through the top sheet 11.

The liquid-pervious top sheet 11 covering the top face side (the side to be in contact with the skin) of the absorber body 13 may preferably be formed of perforated or non-perforated nonwoven fabric or porous plastic sheet. The raw material fibers constituting the nonwoven fabric may be synthetic fibers, such as polyolefin-based including polyethylene or polypropylene, polyester-based, or polyamide-based fibers, recycled fibers, such as rayon or cupra, or natural fibers, such as cotton, and the nonwoven fabric may have been produced through suitable processing, such as spunlacing, spunbonding, thermal bonding, melt-blowing, or needle punching. Among these processing methods, the spunlacing is superior in imparting flexibility and draping properties, whereas the thermal bonding is superior in imparting bulkiness and softness. With a number of through holes formed through the liquid-pervious top sheet 11, urine or the like may rapidly be absorbed, and excellent dry-touch property may be imparted. The liquid-pervious top sheet 11 is folded around the side edges of the absorber body 13 and extends onto the underside thereof.

The liquid-impervious underside sheet 12 covering the under face side (the side out of contact with the skin) of the absorber body 13 may be formed of a sheet of liquid-impervious plastic, such as polyethylene or polypropylene, and those having moisture-permeability are preferably used recently for preventing dampness. Such liquid-impervious, moisture-permeable sheet may be a microporous sheet obtained by kneading an inorganic filler in a polyolefin-based resin, such as polyethylene or polypropylene, in a molten state, forming the resulting mixture into a sheet, and then uni- or biaxially drawing the sheet.

The absorber body 13 may be a commonly-known absorber, for example, an accumulation of pulp fibers, an assembly of filaments, such as of cellulose acetate, or nonwoven fabric, to which a superabsorbent polymer is mixed, fixed, or otherwise, as required. In the illustrated embodiment, an absorber molded into an approximate rectangular shape in plan view is used, with its width being dimensioned not to contact the crotch of the wearer to give coarse touch. The absorber body 13 may be packaged with a liquid-pervious liquid-retaining packing sheet 14, such as of crepe paper, as required, for retaining its shape and holding the polymer therein. The absorber body 13 may be in a rectangular shape as in the illustrated embodiment, or in the shape of an hourglass (centrally narrowed shape) having a narrower crotch section compared to the dorsal and ventral sides.

It is preferred to provide, on each side of the inner member 10, a three-dimensional gather part BS which fits around each leg. Each three-dimensional gather part BS is formed from gather nonwoven fabric 15, which is preferably nonwoven fabric folded into a double sheet as shown in FIGS. 4 and 5, and is folded, together with the liquid-pervious top sheet 11, from the top face side of the absorber body 13 around the side edge thereof to extend and bonded onto the underside of the absorber body 13. More specifically, the gather nonwoven fabric 15 is, in the longitudinal middle portion of the diaper 1, bonded with a hot melt adhesive over the range from the middle portion in the width direction to the portion covering the underside of the absorber body 13, leaving the portion which forms the three-dimensional gather part BS, whereas the gather nonwoven fabric 15 is, in each of the longitudinal front and back end portions, bonded with a hot melt adhesive over the range from the middle portion in the width direction to each lateral side edge covering the underside of the absorber body 13, with the portion which forms the three-dimensional gather part BS, being folded back on the top side of the absorber body 13 and bonded with a hot melt adhesive.

Between the double-sheet nonwoven fabric forming the gather nonwoven fabric 15, a plurality of thread-like elastic members 16 are disposed in the raised edge portion. The thread-like elastic members 16, in the product as shown in chain double-dashed lines in FIG. 4, raise the portion of the nonwoven fabric protruding from a side edge of the absorber body by the elastic stretching/contracting force, to form a three-dimensional gather part BS.

The liquid-impervious underside sheet 12 enters between the double-sheet nonwoven fabric 15 and, as shown in FIG. 4, forms a leak-proof wall on the lower end side of the three-dimensional gather part BS. As such a liquid-impervious underside sheet 12, opaque sheet may preferably be used so that the brown color of feces and urine may not be seen through the sheet. Opaqueness may preferably be imparted by internal addition of pigments or fillers, such as calcium carbonate, titanium oxide, zinc oxide, white carbon, clay, talc, or barium sulfate, to a plastic material, which is followed by formation into a film.

The thread-like elastic members 16 may be made of a material that is usually used, for example, polystyrene rubber, polyolefin rubber, polyurethane rubber, polyester rubber, polyurethane, polyethylene, polystyrene, styrene-butadiene, silicone, or polyester. For poorer external visibility, the thread-like elastic members 16 may have a fineness of 925 dtex or lower, and may be arranged at a stretch rate of 150 to 350% at 7.0 mm or less intervals. In place of the thread-like elastic members, a tape-like elastic member of a certain width may be used.

The raw material fibers constituting the gather nonwoven fabric 15 as discussed above may be, like the liquid-pervious top sheet 11, synthetic fibers, such as polyolefin-based including polyethylene or polypropylene, polyester-based, or polyamide-based fibers, recycled fibers, such as rayon or cupra, or natural fibers, such as cotton, and the nonwoven fabric may have been produced through suitable processing, such as spunbonding, thermal bonding, melt-blowing, or needle punching. In particular, for avoiding dampness, nonwoven fabric with limited basis weight and excellent air permeability may preferably be used. As the gather nonwoven fabric 15, it is preferred to use a water-repellent nonwoven fabric obtained by coating with a silicone, paraffin-metal, or alkyl chromic chloride water-repellent for preventing permeation of urea or the like and for preventing diaper rash and improving the touch (dryness) on the skin <Front and Back Pressor>

As shown in FIGS. 1 and 3, front and back presser sheets 50, 60 are provided for covering the front and back end portions of the inner member 10 attached to the interior surface of the outer member 20, and for preventing leakage through the front and back edges of the inner member 10. Discussing the illustrated embodiment in further detail, the front presser sheet 50 extends over the entire width on the interior surface of the front body section F from the interior surface of the folded-back portion 20C in the waist-side end onto the front end portion of the inner member 10, whereas the back presser sheet 60 extends over the entire width on the interior surface of the back body section B from the interior surface of the folded-back portion 20C in the waist-side end onto the back end portion of the inner member 10. By leaving a small portion of the front/back presser sheet 50, 60 unbonded in its crotch-side edge portion over the entire width (or only in the middle portion), not only the adhesive may not leak out, but also this unbonded portion may be slightly spaced from the top sheet to make it act as a leak-proof wall.

As in the illustrated embodiment, front/back presser sheets 50, 60 separately formed and attached have an advantage of a higher degree of freedom in material choice, but have a disadvantage of increase in the amount of material required or in the manufacturing processes. In view of this, the folded-back portion 20C, which is a portion of the outer member 20 folded back onto the interior surface of the diaper 1, may be extended to partly overlap the absorber body 13, to thereby form a portion equivalent to the presser sheet 50, 60 discussed above.

INDUSTRIAL APPLICABILITY

The present invention may be applied to underpants-type disposable diapers like the embodiment discussed above.

DESCRIPTION OF REFERENCE SIGNS

B: back body section
F: front body section
1: underpants-type disposable diaper
10: inner member
11: liquid-pervious top sheet
12: liquid-impervious underside sheet
13: absorber body
14: packing sheet
15: gather nonwoven fabric
16: thread-like elastic member
20: outer member
20C: folded-back portion
21: side sealed portion
24: waist zone elastic member
25: hip elastic member
26, 28: tortuous elastic member
26: dorsal tortuous elastic member
28: ventral tortuous elastic member
29: around-leg line
B3: area where a larger amount of adhesive is applied
B4: area where a smaller amount of adhesive is applied

The invention claimed is:
1. An underpants-type disposable diaper comprising:
an outer member defining a front body section and a back body section,
wherein opposed lateral side portions of the outer member in the front body section are joined to opposed lateral side portions of the outer member in the back body section by means of ultrasonic bonding or thermal melt-bonding to form opposed lateral side sealed portions, which produce a waist opening and a pair of right and left leg openings, wherein at least one of the front body section and the back body section of the outer member is provided with a tortuous elastic member extending with curvature from one of the side sealed portions to the other of the side sealed portions, and bonded to the outer member with adhesive, wherein the adhesive is applied to a zone neighboring an inner zone of each side sealed portion in a width direction and an outer zone of each side sealed portion in a width direction located on an outer side of the neighboring zone in the width direction, respectively, wherein an amount of adhesive applied to the neighboring zone is larger than an amount of adhesive applied to the outer zone of the each side sealed portion in the width direction, wherein the outer zone of the side sealed portion in the width direction refers to, dividing a width of the side sealed portion into approximate halves, a half which is located on the outer side in the width direction, wherein the neighboring zone is a zone starting from an inner border of the side sealed portion in the width direction, and extending inwards within an extension of 5 to 60 mm in the width direction, and wherein the amount of adhesive refers to a weight per unit area.

2. The underpants-type disposable diaper according to claim 1,
wherein the adhesive is applied to the entire side sealed portion located on the outer side of the neighboring zone in the width direction, and
wherein the amount of adhesive applied to the neighboring zone is larger than an amount of adhesive applied to the entire side sealed portion.

3. The underpants-type disposable diaper according to claim 1, wherein the amount of adhesive applied to the inner zone of the side sealed portion in the width direction and the amount of adhesive applied to the neighboring zone are respectively larger than the amount of adhesive applied to the outer zone of the side sealed portion in the width direction.

4. The underpants-type disposable diaper according to claim 1, wherein the tortuous elastic member is not present in the outer zone of the side sealed portion in the width direction.

5. The underpants-type disposable diaper according to claim 2, wherein the tortuous elastic member is not present in the outer zone of the side sealed portion in the width direction.

6. The underpants-type disposable diaper according to claim 3, wherein the tortuous elastic member is not present in the outer zone of the side sealed portion in the width direction.

* * * * *